(12) United States Patent
Scarborough et al.

(10) Patent No.: US 6,383,221 B1
(45) Date of Patent: May 7, 2002

(54) METHOD FOR FORMING AN INTERVERTEBRAL IMPLANT

(75) Inventors: Nelson L. Scarborough, Ocean; John W. Boyle, Upper Montclair, both of NJ (US)

(73) Assignee: Osteotech, Inc., Eatontown, NJ (US)

( * ) Notice: Subject to any disclaimer, the term of this patent is extended or adjusted under 35 U.S.C. 154(b) by 0 days.

(21) Appl. No.: 09/924,499

(22) Filed: Aug. 8, 2001

Related U.S. Application Data

(62) Division of application No. 09/328,283, filed on Jun. 8, 1999.
(60) Provisional application No. 60/116,852, filed on Jan. 22, 1999.

(51) Int. Cl.⁷ .................................................. A61F 2/44
(52) U.S. Cl. .............................. 623/17.11; 623/23.63; 623/901
(58) Field of Search ....................... 623/17.16, 17.11, 623/17.12, 17.15, 23.63, 901, 925, 17

(56) References Cited

U.S. PATENT DOCUMENTS

| | | | |
|---|---|---|---|
| 4,349,921 A | | 9/1982 | Kuntz |
| 4,714,469 A | * | 12/1987 | Kenna .......................... 623/17 |
| 4,863,477 A | | 9/1989 | Monson |
| 5,047,058 A | | 9/1991 | Roberts et al. |
| 5,112,354 A | * | 5/1992 | Sires ............................ 623/16 |
| 5,306,307 A | | 4/1994 | Senter et al. |
| 5,306,309 A | | 4/1994 | Wagner et al. |
| 5,314,478 A | | 5/1994 | Oka et al. |
| 5,425,772 A | | 6/1995 | Brantigan |
| 5,425,773 A | | 6/1995 | Boyd et al. |
| 5,443,514 A | | 8/1995 | Steffee |
| 5,458,638 A | | 10/1995 | Kuslich et al. |
| 5,458,643 A | | 10/1995 | Oka et al. |
| 5,489,308 A | | 2/1996 | Kuslich et al. |

(List continued on next page.)

FOREIGN PATENT DOCUMENTS

FR   2742652a1   * 6/1997   .............. 623/17.16

OTHER PUBLICATIONS

Vich, Jose M. Otero, Anterior Cervical Interbody Fusion with Threaded Cylindrical Bone, 1985, J. Neurosurg., vol. 63, pp. 750–753.

*Primary Examiner*—Eduardo C. Robert
(74) *Attorney, Agent, or Firm*—Dilworth & Barrese, LLP

(57) ABSTRACT

An intervertebral implant having a composite wedge/dowel configuration is provided. The intervertebral implant includes a central body portion and a pair of radially extending wings. The radially extending wings can be tapered from a first end of the implant to the second end of the implant along an axis parallel to the longitudinal axis of the central body portion. Alternately, the radially extending wings can be tapered along an axis transverse to the longitudinal axis of the cylindrical body portion or along any other axis between parallel and transverse to the longitudinal axis. A throughbore or plurality of throughbores extend from a top surface of the implant through the implant to a bottom surface of the implant. The implant may be formed from a cortical ring cut from the diaphysis of a long bone by milling the top and bottom surfaces of the cortical ring to form the substantially central body portion and the tapered radially extending wings. The cortical ring is milled such that the intramedullary canal of the cortical ring defines a throughbore in the central body portion of the implant. The sidewalls of the implant may be machined to form a substantially rectangular shape or the implant can be left to have a substantially circular configuration. Alternately, the implant may be formed of any biocompatible material having the requisite strength requirements via any known process, i.e., molding.

11 Claims, 10 Drawing Sheets

U.S. PATENT DOCUMENTS

| | | | |
|---|---|---|---|
| 5,507,813 A | * 4/1996 | Dowd et al. | 623/16 |
| 5,514,180 A | 5/1996 | Michelson | |
| 5,522,899 A | 6/1996 | Heggeness et al. | |
| 5,534,028 A | 7/1996 | Bao et al. | |
| 5,534,030 A | 7/1996 | Navarro et al. | |
| 5,554,191 A | 9/1996 | Lahille et al. | |
| 5,562,738 A | 10/1996 | Boyd et al. | |
| 5,571,190 A | 11/1996 | Ulrich et al. | |
| 5,591,235 A | 1/1997 | Kuslich | |
| 5,607,424 A | 3/1997 | Tropiano | |
| 5,645,596 A | 7/1997 | Kim et al. | |
| 5,645,598 A | 7/1997 | Brosnahan, III | |
| 5,653,761 A | 8/1997 | Pisharodi | |
| 5,653,762 A | 8/1997 | Pisharodi et al. | |
| 5,658,336 A | 8/1997 | Pisharodi | |
| 5,658,337 A | 8/1997 | Kohrs et al. | |
| 5,669,909 A | 9/1997 | Zdeblick et al. | |
| 5,683,394 A | * 11/1997 | Rinner | 606/86 |
| 5,683,463 A | 11/1997 | Godefroy et al. | |
| 5,683,464 A | 11/1997 | Wagner et al. | |
| 5,716,415 A | 2/1998 | Steffee | |
| 5,728,159 A | * 3/1998 | Stroever et al. | 623/16 |
| 5,766,251 A | 6/1998 | Koshino | |
| 5,766,252 A | 6/1998 | Henry et al. | |
| 5,769,897 A | 6/1998 | Härle | |
| 5,776,199 A | 7/1998 | Michelson | |
| 5,782,919 A | 7/1998 | Zdeblick et al. | |
| 5,785,710 A | 7/1998 | Michelson | |
| 5,814,084 A | * 9/1998 | Grivas et al. | 623/16 |
| 5,865,845 A | 2/1999 | Thalgott | |
| 5,888,227 A | 3/1999 | Cottle | |
| 5,895,428 A | 4/1999 | Berry | |
| 5,899,939 A | 5/1999 | Boyce, et al. | |
| 5,904,719 A | 5/1999 | Errico et al. | |
| 5,972,368 A | * 10/1999 | McKay | 424/423 |
| 6,123,731 A | * 9/2000 | Boyce et al. | 623/23.63 |
| 6,270,528 B1 | * 8/2001 | McKay | 623/17.11 |

* cited by examiner

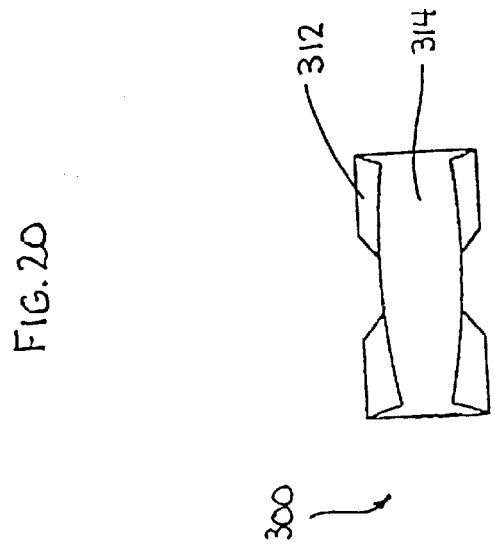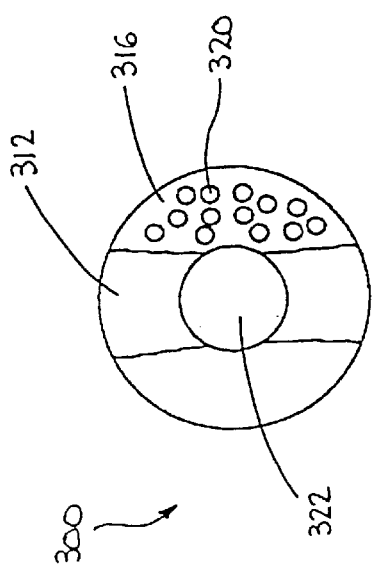

METHOD FOR FORMING AN INTERVERTEBRAL IMPLANT

This application is a divisional of U.S. application Ser. No. 09/328,283 filed Jun. 8, 1999, which claims priority from United States provisional application Ser. No. 60/116,852, filed Jan. 22, 1999, both of which are incorporated herein by reference.

BACKGROUND OF THE INVENTION

1. Technical Field

The present disclosure relates generally to intervertebral implants and, more particularly, to an intervertebral implant having a composite wedge/dowel configuration suitable for interbody spinal fusion.

2. Background of Related Art

Intervertebral implants for fusing together adjacent vertebrae of a spinal column are well known in the surgical arts. Typically, a surgical procedure for implanting an intervertebral implant between adjacent vertebrae is performed to treat back pain in patients with ruptured or degenerated intervertebral discs, spondylolisthesis or other pathologies. A variety of different types of intervertebral implants have been developed for such a procedure including intervertebral wedge implants, spinal fusion cages and cylindrical threaded bone dowels.

A variety of different types of intervertebral implants have been developed to perform this function including spinal fusion cages, threaded bone dowels and stepped bone dowels. Exemplary implants are disclosed in U.S. Patent Applications filed on even date herewith, under Certificate of Express Mail Label Nos. EL260888076US and Intervertebral Dowel", respectively, the entire disclosures of which are incorporated herein by reference.

One fusion cage described in U.S. Pat. No. 5,015,247 includes a cylindrical implant constructed from titanium having one closed end, one open end and a series of macro-sized openings formed through a side wall of the implant. The open end of the cylindrical implant is internally threaded and configured to receive a cap. A series of external threads are formed about the circumference of the cylindrical implant. Prior to use, a bone graft of cancellous bone taken from a patient's iliac crest is placed in a press and forced into the hollow body of the cylindrical implant such that cancerous bone extends through the macro-sized openings. The cap is then screwed onto the internally threaded end of the implant. Subsequently, the cylindrical implant is screwed into a previously prepared receiving bed between two adjacent vertebrae.

Because of their simplicity, spinal fusion cages are widely accepted. However, spinal fusion cages suffer from several drawbacks. For example, the cylindrical loading surface area of spinal fusion cages is small, thus two spinal fusion cages are typically required during a surgical procedure. Secondly, spinal fusion cages are made primarily from metal, most notably titanium. This material does not remodel but remains in a patient forever or until it is removed. Since vertebral bodies eventually fuse with the cancellous bone or other bone growth material positioned within the fusion cage, if removal is required, it can be very difficult and dangerous to the patient. Thirdly, spinal fusion cages do not maintain lordosis, thus the natural curvature of the spine is altered. Finally, it is difficult to insert a spinal fusion cage and achieve equal purchase with the adjacent vertebrae. A spinal fusion cage will often tend to engage one vertebrae more securely than the other.

Wedge implants also suffer from several drawbacks. Although wedge implants have a greater load bearing surface area and are configured to maintain lordosis, wedge implants are more difficult to secure in place since they are not threaded into the vertebrae. Moreover, wedge implants have limited ability to prevent rotational forces between the two vertebrae that are intended to be fused.

Threaded bone dowels also suffer from some of the same drawbacks as spinal fusion cages. Threaded bone dowels have a small loading surface area and they do not maintain lordosis. Furthermore, threaded bone dowels are typically cut from bone with a hollow drill bit and subsequently are threaded. The hollow drill bit is positioned to cut transversely through the bone and the intramedullary canal during the cut. If the distance between the outer surface of the cut dowel and the intramedullary canal does not exceed a predetermined thickness, the dowel must be rejected. Since there is little bone to spare during such a transverse cut, a high percentage of bone dowels cut may be rejected due to anatomical variability between donors.

Accordingly, a need exists for an improved intervertebral implant which maintains simplicity for consistent surgical implantation, creates an improved biomechanical construct when implanted, maintains lordosis, conforms to vertebral endplates, spares the endplates in the load bearing region while perforating them in other areas to gain access to cells in cancellous bone; when produced from bone, can remodel into bone, can be easily manufactured and addresses other problems associated with current spinal fusion implants.

SUMMARY

In accordance with the present disclosure, an intervertebral implant having a composite wedge/dowel configuration is provided. The intervertebral implant includes a central body portion and a pair of radially extending wings. The radially extending wings can be tapered from a first end of the implant to the second end of the implant along an axis parallel to the longitudinal axis of the cylindrical body portion for anterior or posterior insertion. Alternately, the radially extending wings can be tapered along an axis perpendicular to the longitudinal axis of the cylindrical body portion for lateral insertion or the wings can be tapered along any axis between axis parallel and perpendicular to the longitudinal axis of the implant. A throughbore or a plurality of throughbores extend from a top surface of the implant to a bottom surface of the implant providing a space for boney bridging to occur between the vertebrae which are intended to be fused. The throughbore(s) is dimensioned to receive growth factors including autograft, allograft, DBM, etc., to stimulate bone healing.

In a preferred embodiment, the implant is formed from a cortical ring allograft cut from the diaphysis or metaphysis of a long bone. The implant can be formed by milling the top and bottom surfaces of the cortical ring to form the central body portion and the tapered radially extending wings. The implant is milled such that the intramedullary canal of the cortical ring defines a throughbore in the central body portion of the implant. Thereafter, the sidewalls of the implant may be machined to form a substantially rectangular shape or be maintained in an essentially semi-circular configuration. Alternately, the implant may be formed of any biocompatible material having the requisite strength requirements via any known process, i.e., molding, casting, machining, etc.

BRIEF DESCRIPTION OF THE DRAWINGS

Various preferred embodiments are described herein with reference to the drawings wherein:

FIG. 19 is a perspective view of a sixth embodiment of the presently disclosed intervertebral implant;

FIG. 20 is a front view of the intervertebral implant shown in FIG. 19;

FIG. 21 is a top view of the intervertebral implant shown in FIG. 19;

FIG. 22 is a side view of the intervertebral implant shown in FIG. 19;

DETAILED DESCRIPTION OF PREFERRED EMBODIMENTS

Figure 1:
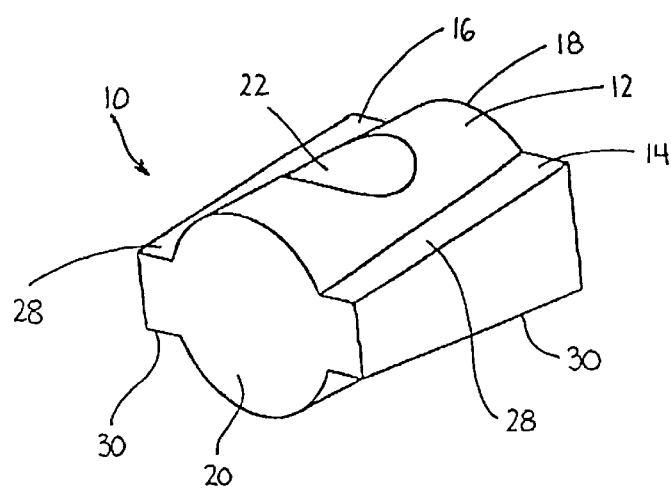
FIG. 1 is a perspective view of one embodiment of the presently disclosed intervertebral implant.
Figure 2:
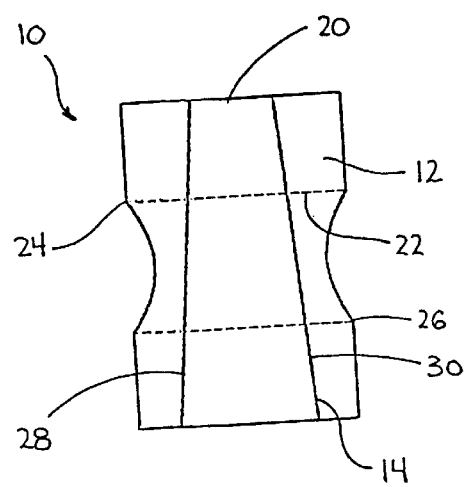
FIG. 2 is a side view of the intervertebral implant shown in FIG. 1.
Figure 3:
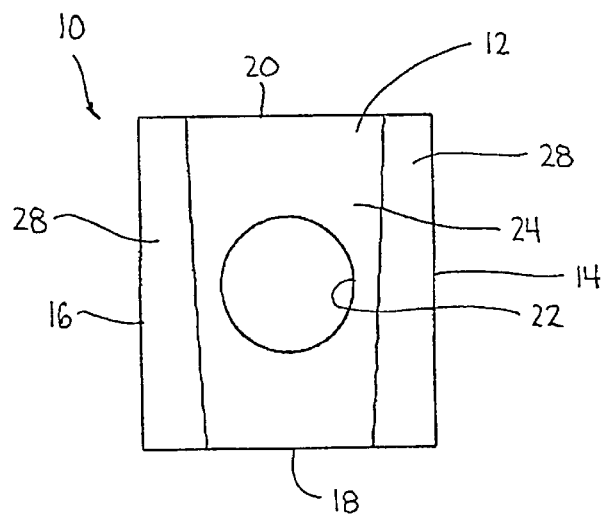
FIG. 3 is a top view of the intervertebral implant shown in FIG. 1.
Figure 4:
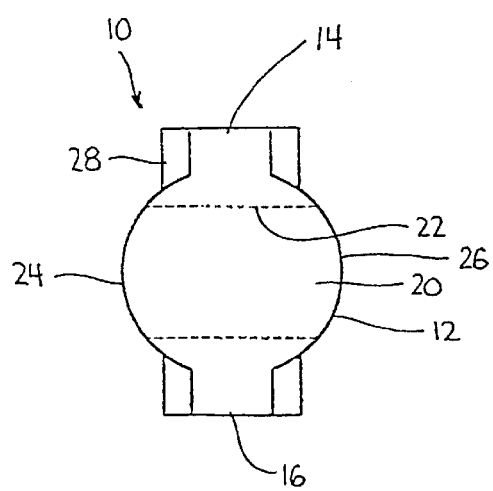
FIG. 4 is a front view of the intervertebral implant shown in FIG. 1.
Figure 5:
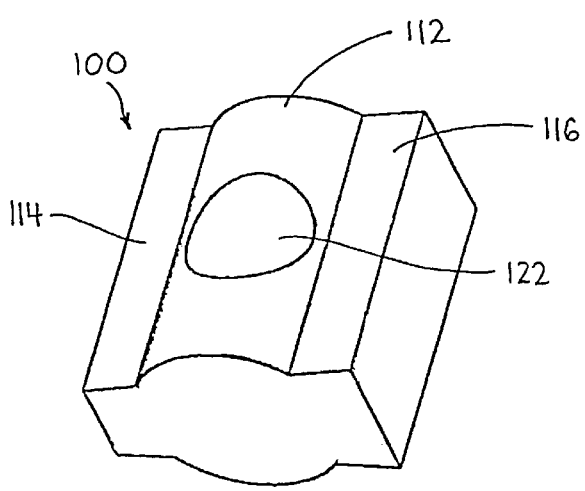
FIG. 5 is a perspective view of another embodiment of the presently disclosed intervertebral implant.
Figure 6:
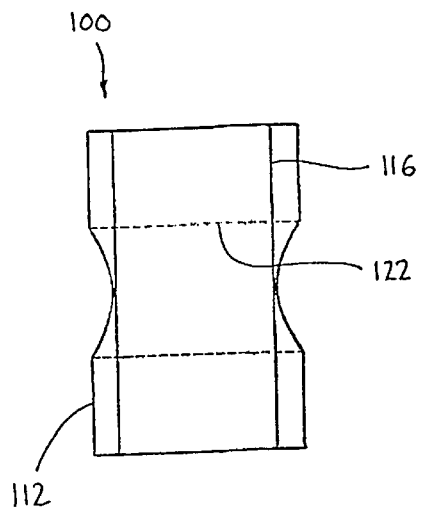
FIG. 6 is a side view of the intervertebral implant shown in FIG. 5.
Figure 7:
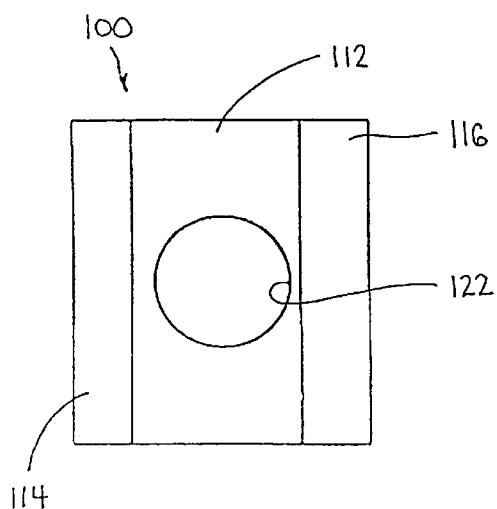
FIG. 7 is a top view of the intervertebral implant shown in FIG. 5.
Figure 8:
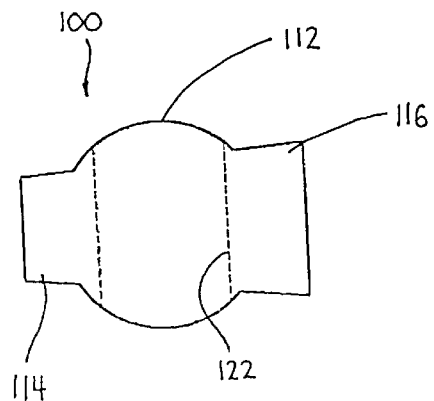
FIG. 8 is a front view of the intervertebral implant shown in FIG. 5.

Preferred embodiments of the presently disclosed intervertebral implant will now be described in detail with reference to the drawings, in which like reference numerals designate identical or corresponding elements in each of the several views.

FIGS. 1–4 illustrate one preferred embodiment of the presently disclosed intervertebral implant shown generally as 10. Briefly, intervertebral implant 10 includes a substantially cylindrical body portion 12 having a pair of radially extending wings 14 and 16. Cylindrical body portion 12 has a first end 18 and a second end 20. Each of radially extending wings 14 and 16 has a trapezoidal shape as viewed from the side of intervertebral implant 10.

Cylindrical body portion 10 includes a throughbore 22 which extends from a top surface 24 of body portion 12 to a bottom surface 26 of body portion 12. Throughbore 22 has a central axis which is perpendicular to the longitudinal axis of radially extending wings 14 and 16 and cylindrical body portion 10. Throughbore 22 is dimensioned to receive bone growth material including bone particles and/or a biocompatible osteoinductive or osteoconductive material. These materials may include cancellous bone, cancellous bone particles, ceramics, polymers, composites, BMP, etc. Although not shown, additional bores may be formed through wings 14 and 16. These bores may also be packed with bone growth material.

Radially extending wings 14 and 16 each include an upper surface 28 and a lower surface 30. Surfaces 28 and 30 are tapered to converge toward each other from first end 18 of cylindrical body portion 12 to second end 20 of cylindrical body portion 12, i.e., the height of the wings decreases from the first end to the second end of the implant. The wings are shaped in such a fashion as to conform to the vertebral end plates located above and below the implant. Implant 10 is suitable for anterior and posterior insertion. Alternately, surfaces 28 and 30 may be parallel to each other.

Intervertebral implant 10 can be constructed from a broad range of biocompatible materials, such as surgical stainless steel, titanium, ceramic hydroxyopatite, polymers, carbon fiber tantalum, etc., but is preferably constructed from cadaveric human or animal bone or bone composites. Such composites may include those discussed in U.S. Pat. No. 5,899,939 to Boyce et al. and in U.S. patent application Ser. No. 09/256,447 to Boyce et al., the entire disclosures of which are incorporated herein by reference. Intervertebral implant 10 can be used in cervical, thoracic and lumbar spinal fusion procedures. For cervical spinal fusion procedures, in which implants are typically between 8–15 mm in length and 10–14 mm in diameter, bone is preferably obtained from the fibula, radius, ulna or humerus. For thoracic and lumbar spinal fusion procedures in which implants are typically 10–30 mm in diameter and about 14–20 mm in height, bone is preferably obtained from the humerus, femur or tibia. Alternately, as discussed above, intervertebral implant 10 can be molded or machined from other biocompatible materials including composites made of bone.

Figure 9:
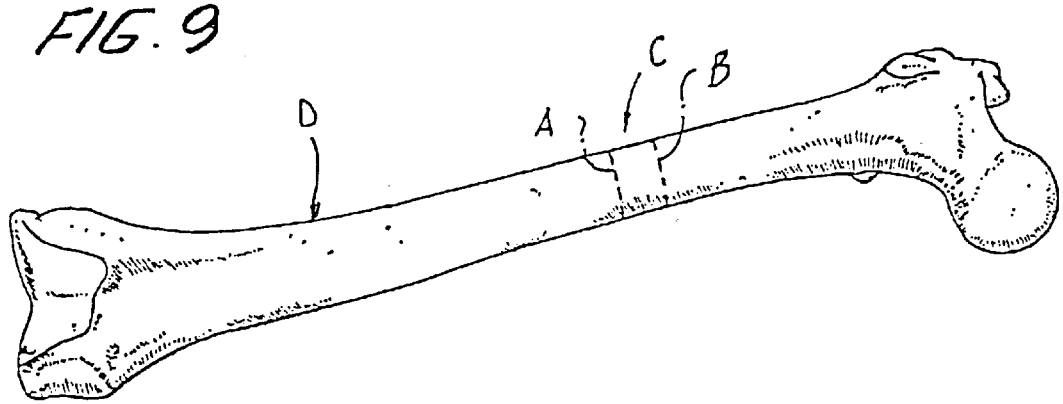
FIG. 9 is a side view of a long bone.
Figure 10:
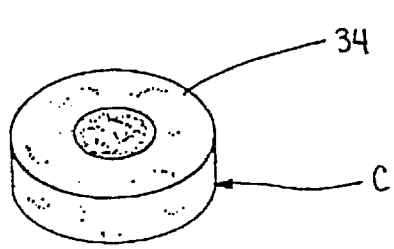
FIG. 10 is a perspective view of a cortical ring cut from the long bone shown in FIG. 9.
Figure 11:
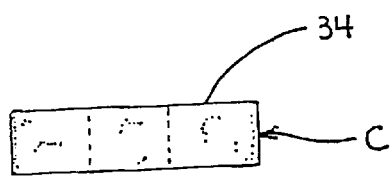
FIG. 11 is a side view of the cortical ring shown in FIG. 10.
Figure 12:
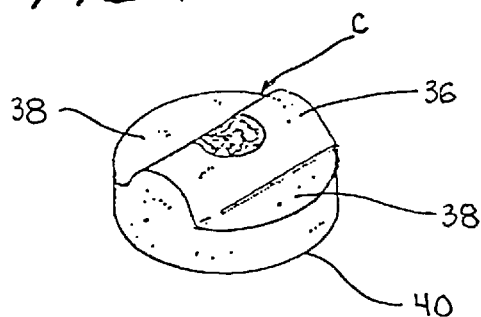
FIG. 12 is a perspective view of the cortical ring after the top surface has been milled.
Figure 13:
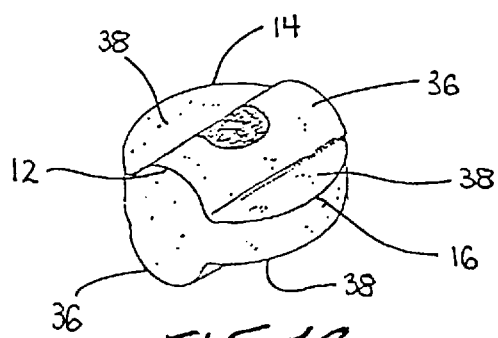
FIG. 13 is a perspective view of the cortical ring after the bottom surface has been milled.
Figure 14:
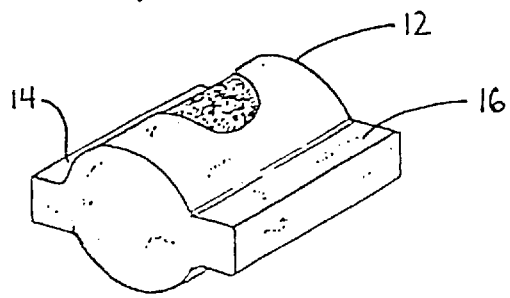
FIG. 14 is a perspective view of the cortical ring after the sidewalls have been machined.
Figure 15:
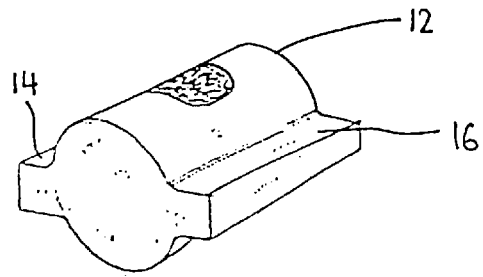
FIG. 15 is a perspective view of the cortical ring after the radially extending wings have been tapered.

Referring to FIGS. 9–15 above, in one preferred embodiment, intervertebral implant 10 is manufactured from a cortical ring C formed by making transverse cuts through a long bone D, along lines A and B as illustrated in FIG. 9. Next, the top 34 of cortical ring C is machined using a milling device (not shown) having a dome or crown configuration to shape one side of cortical ring C to have a semi-cylindrical portion 36 with two radially extending flats 38 (FIG. 12). Cortical ring C is flipped over and the same milling procedure is performed on the bottom surface 40 to form radially extending wings 14 and 16 and cylindrical body portion 12. Next, the front and side surfaces are machined to reconfigure cortical ring C to have a rectangular configuration (FIG. 14). Alternately, this step may be deleted and the implant can retain its original profile which will vary depending on the type of bone being cut. Finally, wings 14 and 16 are machined further to provide the taper required to maintain lordosis of the spine (FIG. 15). Each of the milling steps may be performed independently using any known milling device. However, one or more of the steps may be combined into a single milling procedure using a computer controlled three dimensional milling machine. For example, radially extending wings 14 and 16 can be tapered during milling of the top and bottom surfaces of the cortical ring.

Preferably, before long bone D is cut, the bone is partially demineralized by placing the long bone in a 0.6NHCl solution. By demineralizing the bone in this fashion, only the walls of the intramedullary canal and the circumferential surfaces of the bone may be demineralized. The strength imparting surfaces of the radially extending wings and the radial surface of the implant will not be compromised. Moreover, the bone may be treated using a variety of bone healing enhancing technologies. For example, bone growth factors may be infused into the natural porosity of the bone and/or the bone may be infused with acid to further demineralize the bone. Both these bone treatments may be performed using the pressure flow system disclosed in U.S. Pat. No. 5,846,484 which is incorporated herein by reference.

As discussed above, intervertebral implant 10 need not be formed from human cadaveric or animal bone but rather may be formed from any biocompatible material. As such, other known processes, such as molding, casting or machining techniques, may be used to manufacture the implant.

FIGS. 5–8 illustrate another embodiment of the intervertebral implant shown generally as 100. Intervertebral implant 100 is similar to intervertebral implant 10 in that it includes a cylindrical body portion 112, a pair of radially extending wings 114 and 116 and a throughbore 122 having a central axis which is perpendicular to the longitudinal axis of the radially extending wings and cylindrical body portion. However, radially extending wings 114 and 116 are tapered transversely such that wing 116 has greater height than wing 114. Implant 100 is suitable for lateral intervertebral insertion.

Intervertebral implant 100 may be manufactured using the same procedure as discussed above with respect to intervertebral implant 10 with slight variation in the milling step for forming the taper on the radially extending wings. Alternately, intervertebral implant 100 may be formed from a biocompatible material having the requisite strength requirements via any known process, i.e., molding, casting or machining.

Figures 16, 17:
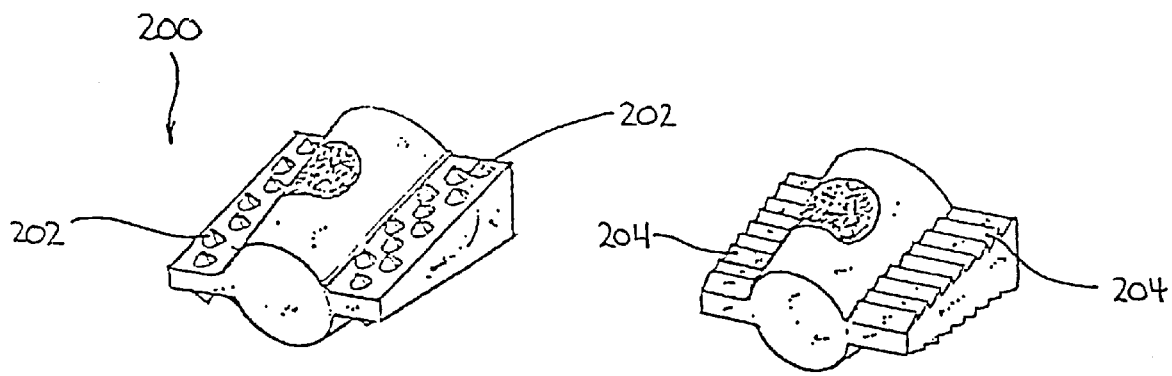
FIG. 16 is a perspective view of a third embodiment of the presently disclosed intervertebral implant.
FIG. 17 is a perspective view of a fourth embodiment of the presently disclosed intervertebral implant.
Figure 18:
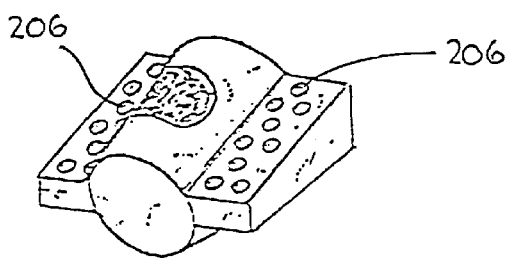
FIG. 18 is a perspective view of a fifth embodiment of the presently disclosed intervertebral implant.

Referring to FIGS. 16–18, intervertebral implants 10 and 100 may include retaining structure for preventing the implant from migrating from an implanted position after implantation. For example, intervertebral implant 200 (FIG. 16) includes a plurality of triangular protrusions 202 formed on the tapered surfaces of the radially extending wings. Protrusions 202 engage the adjoining vertebrae and prevent the implant from movement in relation thereto. Alternately, the protrusions may assume a variety of different configurations. For example, ridge-shaped protrusions 204 (FIG. 17) or spherically-shaped protrusions 206 (FIG. 18) may also be provided. Perforations (not shown) for receiving bone growth material may also be provided on the outer surface of the implant. It is noted that such protrusions or perforations may also be provided on the cylindrical body portion of the intervertebral implant.

Figure 18A:
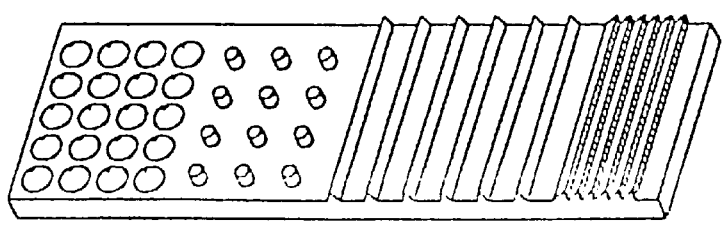
FIG. 18a is a perspective view of a variety of different shaped protrusions.
Figure 24:
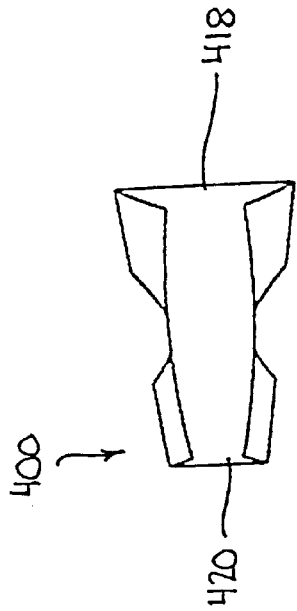
FIG. 24 is a side view of the intervertebral implant shown in FIG. 23.
Figure 26:
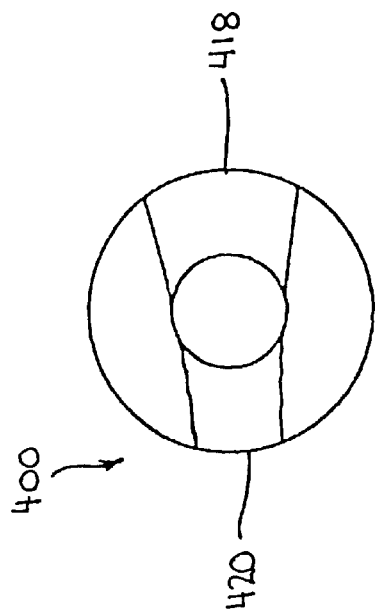
FIG. 26 is a top view of the intervertebral implant shown in FIG. 23.
Figure 23:
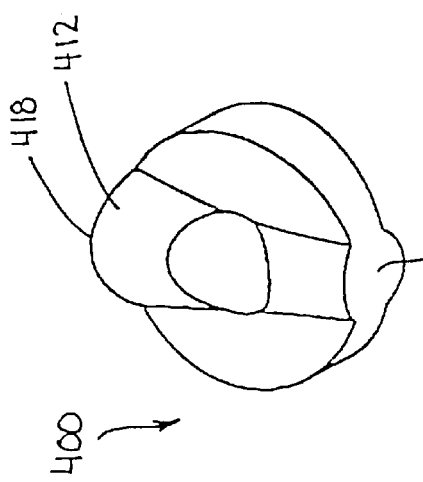
FIG. 23 is a perspective view of a seventh embodiment of the presently disclosed intervertebral implant.
Figure 25:
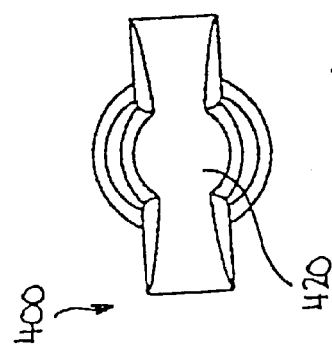
FIG. 25 is a front view of the intervertebral implant shown in FIG. 23.
Figure 28:
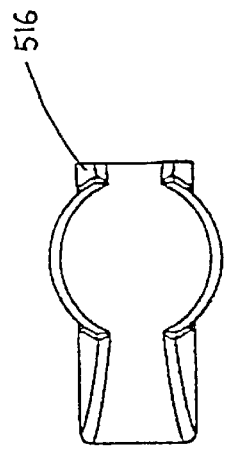
FIG. 28 is a side view of the intervertebral implant shown in FIG. 27.
Figure 30:
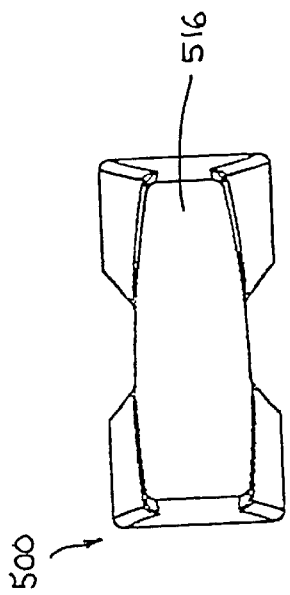
FIG. 30 is a side view of the intervertebral implant shown in FIG. 27.
Figure 27:
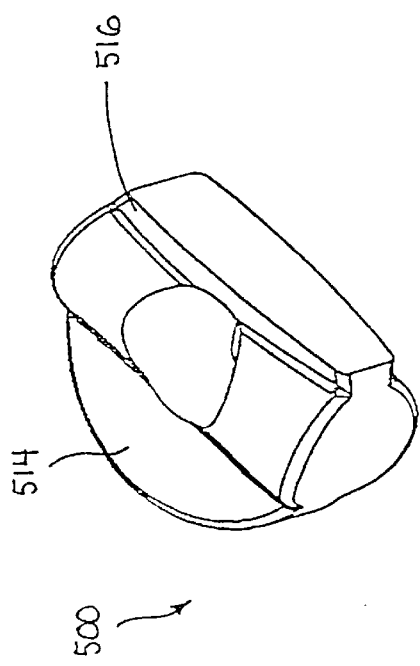
FIG. 27 is a perspective view of an eighth embodiment of the presently disclosed intervertebral implant.
Figure 29:
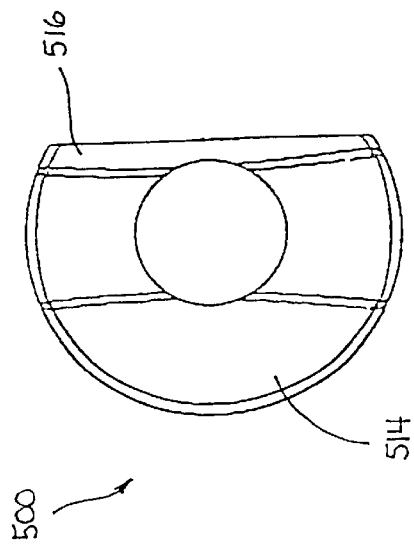
FIG. 29 is a top view of the intervertebral implant shown in FIG. 27.
Figure 31:
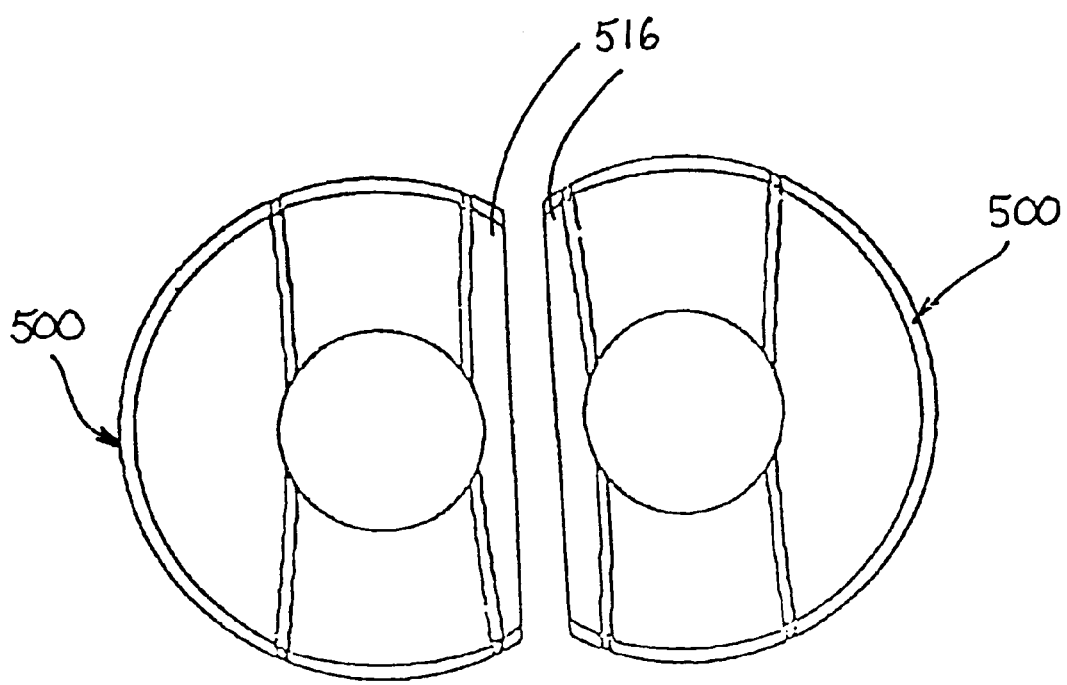
FIG. 31 is a top view of a pair of the intervertebral implants shown in FIG. 27 in their implanted positions.

FIG. 18a illustrates a variety of different protrusions which may be formed anywhere on the implant to prevent the implant from migrating from its implanted position in the intervertebral space.

FIGS. 19–22 illustrate an alternate embodiment of the presently disclosed intervertebral implant shown generally as 300. Intervertebral implant 300 includes a substantially cylindrical body portion 312 having a pair of radially extending wings 314 and 316. Radially extending wings 314 and 316 have a substantially semi-circular shape and have a height which decreases from a first end to a second end of the implant. A series of holes 320 are formed in wing 316 and a throughbore 322 extends through cylindrical body portion 312. Each of holes 320 and throughbore 322 is configured to receive bone growth material, as discussed above. Alternately, holes 320 may be formed in both radially extending wings 314 and 316.

Referring to FIGS. 23–26, the intervertebral implant, shown generally as 400, may include a substantially conical body portion 412. See also FIGS. 16–18. Conical body portion 412 decreases in height from first end 418 to second end 420 of the implant.

Referring to FIGS. 27–31, the intervertebral implant, shown generally as 500, may include only one radially extending wing 514. The other radially extending wing 516 can be either partially or completely eliminated. As illustrated in FIGS. 27–30, radially extending wing 516 has been truncated. During a surgical procedure in which two intervertebral implants are implanted between adjoining vertebrae, the side of each implant having the truncated wing (or the side from which the implant has been eliminated) is positioned adjacent to the truncated wing of the other implant. See FIG. 31.

Figure 32:
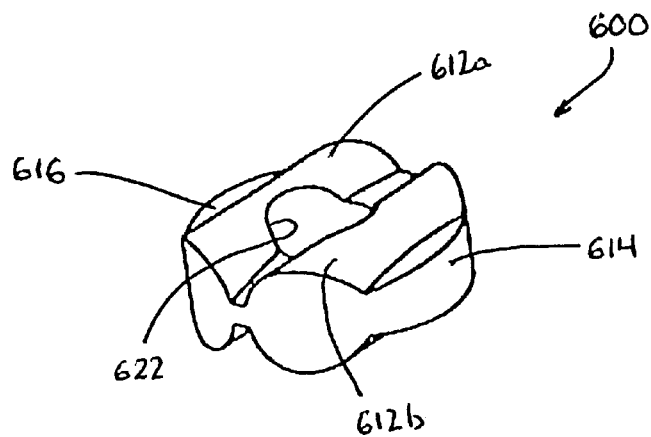
FIG. 32 is a perspective view of another embodiment of the intervertebral implant.

FIG. 32 illustrates another embodiment of the intervertebral implant shown generally as 600. Intervertebral implant 600 includes a pair of cylindrical body portions 612a and 612b, a pair of radially extending wings 614 and 616, a central body portion 618 and a throughbore 622. Throughbore 622 is centrally located in implant 600 and extends through a portion of both cylindrical body portions 612a and 612b. A single implant 600 can be used in surgical procedures which typically required two intervertebral implants such as that shown in FIG. 31.

FIGS. 33–36 illustrate another embodiment of the intervertebral implant shown generally as 700. Implant 700 includes a substantially cylindrical body portion 712 having a pair of radially extending semi-circular wings 714 and a throughbore 722. The top and bottom surfaces 724 and 726 of wings 714 are convex to conform to the anatomical shape of the vertebral end plates. Alternately, the top and bottom surfaces of the wings may assume other shapes which conform to the shape of the vertebral endplates. Implant 700 further includes a slot 750 and a threaded bore 752. Threaded bore 752 extends from slot 750 into throughbore 722. Slot 750 and threaded bore 752 are configured to engage an implant insertion tool (not shown) to facilitate insertion of the implant into the intervertebral space. Although the slot and threaded bore are not shown in combination with the other implants disclosed in this application, it is contemplated that each of the implants disclosed herein may include such insertion tool engaging structure.

Figure 37:
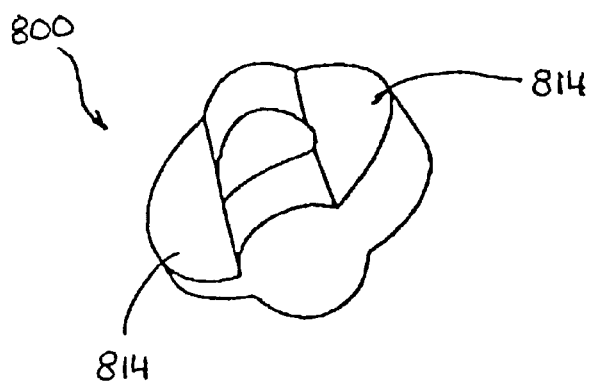
FIG. 37 is a front perspective view of another embodiment of the intervertebral implant.
Figure 38:
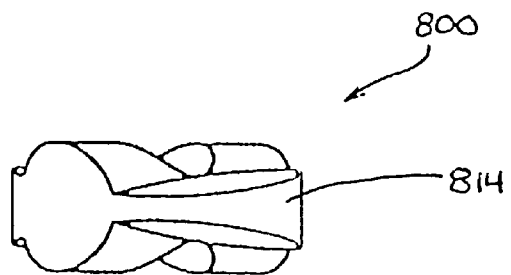
FIG. 38 is a side perspective view of the intervertebral implant shown in FIG. 37.
Figure 33:
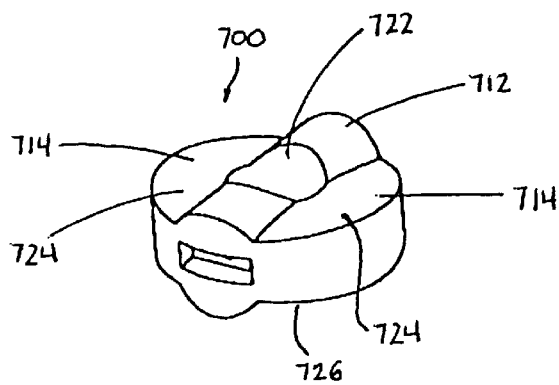
FIG. 33 is a perspective view of another embodiment of the intervertebral implant.
Figure 34:
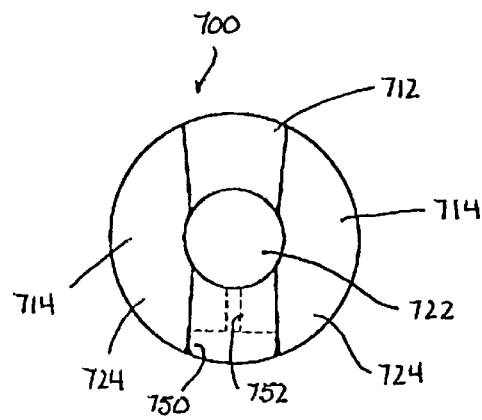
FIG. 34 is a top view of the intervertebral implant shown in FIG. 33.
Figure 35:
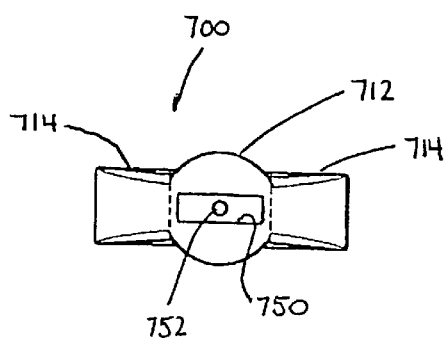
FIG. 35 is a front view of the intervertebral implant shown in FIG. 33.
Figure 36:
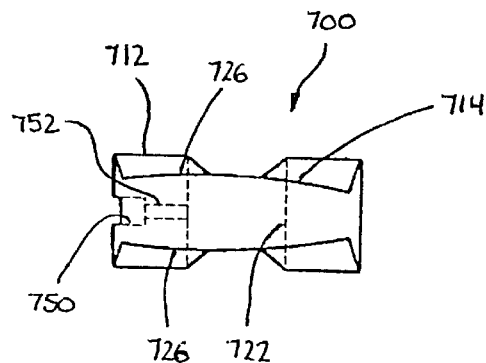
FIG. 36 is a side view of the intervertebral implant shown in FIG. 33.

It will be understood that various modifications may be made to the embodiments disclosed herein. For example, radially extending wings have been described as being tapered or angled along axis both parallel and transverse to the longitudinal axis of the implant. Alternately, radially extending wings can be tapered along any axis between the parallel and transverse axis. For example, radially extending wings 814 of implant 800 are tapered along an axis which forms an angle of about 45° with respect to the longitudinal axis of the cylindrical body portion 812. See FIGS. 37 and 38. Moreover, the taper of the radially extending wings may be different than that shown but should be such as to maintain the natural alignment of the vertebrae. Alternately, radially extending wings need not be tapered. Therefore, the above description should not be construed as limiting, but merely as exemplifications of preferred embodiments. Those skilled in the art will envision other modifications within the scope and spirit of the claims appended hereto.

What is claimed is:

1. A method for forming an intervertebral implant from a diaphysis or metaphysis of a long bone comprising the following steps:

a. making a transverse cut across a long bone to form a cortical ring;

b. milling a top surface of the cortical ring to form a first longitudinally extending crown having two upper radially extending flats; and c. milling a bottom surface of the cortical ring to form a second longitudinally extending crown having two lower radially extending flats, the upper and lower flats forming a pair of radially extending wings.

2. A method according to claim 1, wherein the first and second crowns are milled to form a substantially cylindrical body portion.

3. A method according to claim 2, wherein the first and second crowns are milled such that an intramedullary canal of the long bone extends through the substantially cylindrical body portion.

4. A method according to claim 3, further including the steps of:

milling the side surfaces of the cortical ring to form a substantially rectangular implant.

5. A method according to claim 2, further including the step of milling the upper and lower radially extending flats to vary an angle of the flats in a direction parallel to a longitudinally extending axis of the substantially cylindrical body portion.

6. A method according to claim 2, further including the step of milling the upper and lower radially extending flats to vary an angle of the flats in a direction transverse to a longitudinal axis of the cylindrical body portion.

7. A method according to claim 1, further including the following step:

d. forming protrusions on the intervertebral implant.

8. A method according to claim 7, wherein the protrusions are formed on the radially extending wings.

9. A method according to claim 1, wherein the first and second crowns are milled to form a substantially conical body portion.

10. A method according to claim 1, further including the step of forming at least one hole in at least one of the radially extending wings.

11. A method according to claim 1, wherein at least one of the upper and lower flats defining each of the radially extending wings is convex.

\* \* \* \* \*